(12) United States Patent
Gumbrecht et al.

(10) Patent No.: US 7,488,578 B2
(45) Date of Patent: Feb. 10, 2009

(54) METHOD FOR DETECTING DNA POINT MUTATIONS (SINGLE NUCLEOTIDE POLYMORPHISM (SNP) ANALYSIS) AND ASSOCIATED ARRANGEMENT

(75) Inventors: Walter Gumbrecht, Herzogenaurach (DE); Peter Paulicka, Erlangen (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 15 days.

(21) Appl. No.: 10/558,709

(22) PCT Filed: May 28, 2004

(86) PCT No.: PCT/EP2004/005829

§ 371 (c)(1),
(2), (4) Date: Nov. 13, 2006

(87) PCT Pub. No.: WO2004/106546

PCT Pub. Date: Dec. 9, 2004

(65) Prior Publication Data

US 2007/0264630 A1    Nov. 15, 2007

(30) Foreign Application Priority Data

May 30, 2003   (DE) ................. 103 24 912

(51) Int. Cl.
C12Q 1/68     (2006.01)
C07H 21/02    (2006.01)
C07H 21/04    (2006.01)

(52) U.S. Cl. ................ 435/6; 536/23.1; 536/24.3

(58) Field of Classification Search .......... 435/6; 536/23.1, 24.3

See application file for complete search history.

(56) References Cited

U.S. PATENT DOCUMENTS

| | | | |
|---|---|---|---|
| 5,089,387 A | 2/1992 | Tsay et al. | |
| 5,965,410 A | 10/1999 | Chow et al. | |
| 6,255,677 B1 | 7/2001 | Caillat et al. | |
| 6,391,558 B1 | 5/2002 | Henkens et al. | |
| 2002/0012932 A1 | 1/2002 | Wang | |
| 2002/0037530 A1 | 3/2002 | Stewart et al. | |
| 2002/0098484 A1 | 7/2002 | Shriver et al. | |
| 2003/0087242 A1 | 5/2003 | Mirkin et al. | |
| 2003/0091477 A1 | 5/2003 | Paul et al. | |

FOREIGN PATENT DOCUMENTS

| | | | |
|---|---|---|---|
| DE | 101 11 420 A1 | 9/2002 | |
| WO | WO 98/08083 A1 | 2/1998 | |
| WO | WO 99/67628 A1 | 12/1999 | |
| WO | WO 00/11473 A1 | 3/2000 | |
| WO | WO 01/23600 A2 | 4/2001 | |
| WO | WO 02/083952 A1 | 10/2002 | |
| WO | WO 02/086162 A1 | 10/2002 | |

OTHER PUBLICATIONS

Hanbin Mao, et al.: "Reusable Platforms for High-Throughput On-Chip Temperature Gradient Assays", Anal. Chem. 2002, vol. 74; S. 5071-5075.
Wen-Tso Liu et al.: "Optimization of an oligonucleotide microchip for microbial identification studies: a non-equilibrium dissociation approach", Environmental Microbiology (2001) 3 (10), S. 619-629.
Alexander V. Fotin et al.: Parallel thermodynamic analysis of duplexes on oligodeoxyribonucleotide microchips, Nucleic Acids Research, 1998, vol. 26, No. 6, S. 1515-1521.
Said El Fantroussi et al: "Direct Profiling of Environmental Microbial Populations by Thermal Dissociation Analysis of Native rRNAs Hybridized to Oligonucleotide Microarrays", Applied and Environmental Microbiology, Apr. 2003, S. 2377-2382.
V.R.Chechetkin et al.: "Sequencing by Hybridization with the Generic 6-mer Oligonucleotide Microarray : An Advanced Scheme for Data Processing", Journal of Biomolecular Structure & Dynamics, vol. 18, Issue No. 1 (2000), S. 83-101.
Gerome Breen: "Novel and alternate SNP and genetic technologies", Psychiatric Genetrics 12, S. 83-88.
Jodi L. Kawagoe et al: "Enzyme-Modified Organic Conducting Salt Microelectrode", Analytical Chemistry 63 (Dec. 15, 1991), No. 24, Washington, DC, US.

(Continued)

*Primary Examiner*—Ethan Whisenant
(74) *Attorney, Agent, or Firm*—Harness, Dickey & Pierce, P.L.C.

(57) ABSTRACT

The single nucleotide polymorphism analysis involves the utilization of a DNA hybridization process as well as the use of a DNA chip. A liquid DNA sample to be analyzed is guided over a DNA chip in a defined time course. After successful hybridization, the temperature is modified in a defined manner under low stringency conditions such that scavenger/target DNA hybrids are melted, whereby the melting of the scavenger/target DNA hybrids is detected and evaluated according to the temperature. In addition to the DNA chip, at least one device is provided that controls and regulates the temperature, and another device is provided that controls a lateral flow of liquid against the surface of the DNA chip. Factors for matching hybrids and mismatching/single point mismatching hybrids can be detected and evaluated using appropriate measuring device(s).

23 Claims, 5 Drawing Sheets

OTHER PUBLICATIONS

Philip S. Bernard et al. "Ingtegrated Amplification and Detection of the C677T Point Mutation in the Methylenetetrahydrofolate Reductase Gene by Fluorescence Resonance Energy Transfer and Probe Melting Curves", Analytical Biochemistry 255,S. 101-107 (1998), Article No. AB972427.

F. Pariente et al.: "Enzyme support systems for biosensor applications based on gold-coated nylon meshes", Biosensors & Bioelectronics, vol. 11, No. 11, S. 1115-1128, 1996.

J.P. Cloarec et al.: "Immobilization of homooligonucleotide probe layers onto Si/SiO2 substrates : characterization by electrochemical impedance measurements and radiolabelling", Biosensos & Bioelectronics 17 (2002), S. 405-412.

Dilsat Ozkan: "Allele-Specific Genotype Detection of Factor V Leiden Mutation from Polymerase Chain Reaction Amplicons Bases on Label-Free Electrochemical Genosensors".

Takahiko Nojima et al.: "Direct Detection of Single Nucleotide Polymorphism (SNP) with Genomic DNA by the Ferrocenylnaphthalene Diimide-based Electrochemical Hybridization Assay (FND-EHA)", Analytical Sciences Jan. 2003, vol. 19, S. 79-83.

J. Hassmann et al.: "Development of a molecular diagnosis assay based on electrohybridization at plastic electrodes and subsequent PCR", Biosensors & Bioelectronics 16 (2001), S. 857-863.

Yuk Foi Leung and Chi Pui Pang: "All aboard the chip!", Trends in Biotechnolgy, vol. 19 , No. 11, 2001.

E.Souteyrand et al.: Comparison Between Electrochemical and Optoelectrochemical Impedance Measurements for Detection of DNA Hybridization, Applied Biochemistry and Biotechnolgy, vol. 89, 2000, S. 195-207.

K.L.Dudeck et al: "Phlyogenic Molecular-Based Methods", ASM 101st General Meeting, Orlando, Florida, Session No. 71/N, Abstract N-94, May 21, 2001.

Hidetoshi Urakawa et al., "Optimization of Single-Base-Pair Mismatch discrimination in oligonucleotide microarrays", Applied and Environmental Microbiology, May 2003.

Kawagoe J.L. et al., "Enzyme-Modified Organic Conducting Salt Microelectrode" Analytical chemistry, American chemical Society, Dec. 15, 1991.

METHOD FOR DETECTING DNA POINT MUTATIONS (SINGLE NUCLEOTIDE POLYMORPHISM (SNP) ANALYSIS) AND ASSOCIATED ARRANGEMENT

This application is the national phase under 35 U.S.C. § 371 of PCT International Application No. PCT/EP2004/005829 which has an International filing date of May 28, 2004, which designated the United States of America and which claims priority on German Patent Application number DE 103 24 912.5 filed May 30, 2003, the entire contents of which are hereby incorporated herein by reference.

FIELD

The invention generally relates to a method for detecting DNA point mutations (SNP analysis); for example utilizing a binding (hybridization) of target DNA to be detected to capture DNA which is immobilized position-specifically on a DNA chip.

BACKGROUND

DNA analysis by use of a hybridization technique, is a known method (in "Gentechnische Methoden" G. Gassen and G. Schrimpf, Spektrum Akademischer Verlag Heidelberg, 1999, Chapter 11 "Blottingverfahren und Hybridisierungen", pages 243 to 261). DNA probe molecules, called capture oligonucleotides, which, because of their specific affinity for the complementary sample DNA, "capture" the latter by forming so-called hybrids, i.e. pairs of capture molecule and target molecule, are immobilized on a solid support material. This binding event is normally indicated by optical or else enzymatic reporter molecules.

Such DNA analyses are used for example to detect infectious agents, such as tuberculosis or HIV. DNA analysis must satisfy a particular requirement in the case of so-called single nucleotide polymorphism, SNPs for short. It is necessary here for a capture molecule consisting of about 20 different nucleotides to bind selectively or not bind target molecules which differ in only a single nucleotide. Since the differences in binding energy are very small, the requirements to be met by the selectivity of the DNA sensor are very high.

DNA sensors are known in the art, reference being made for example to the non-prior-published DE 102 59 820 A1 and DE 102 59 821 A1 of the applicant. The formation of the capture/target DNA hybrids takes place under specific boundary conditions, where matching capture/target DNA pairs have a higher binding energy than those having a base mismatch. Because of the small differences in binding energy in SNPs, it is often not possible to distinguish unambiguously a perfect match and a single point mismatch.

A latter problem has to date been solved by introducing a so-called stringent washing step in the prior art analytical methods, i.e. the ionic strength of a washing liquid was chosen so that the initially nonspecifically bound single base mismatch target molecules are separated from the captors, but the perfect match target molecules remain bound to the capture molecules. Even more elaborate optical melting point analyses are likewise possible.

In this method, use is made of the intrinsic change in the light absorption when the DNA double strand melts, and no optical label is necessary. Both with stringent washing and in the optical melting point analysis, in which moreover relatively large amounts of DNA are required and a spectrophotometer is indispensable for detection in liquid phase, it is usually possible for the conditions to be set for only a single SNP. If a plurality of SNPs are present on a sensor chip, separation of all the mismatches is impossible.

In the optical detection of melting curves, the optical signal (intrinsic activity of the DNA, or label) often does not have the stability required for continuous measurements or repeat measurements. The same applies to irreversible detection methods. In particular, it may be necessary for the chip to be dried after the stringent washing before it can be passed on for optical reading.

In "An Active Microelectronics Device for Multiplex DNA Analysis", M. Heller, IEEE Engineering in Medicine and Biology, March/April 1996, pages 100 to 104 there is further a description of a so-called "electrical stringency treatment" in which the hybridization is carried out on a chip provided with electrodes. Single point mismatch hybrids are separated owing to the polyanionic character of the DNA through a negative polarization of the electrodes.

This method has, however, not been able, to establish itself as a robust and general method. Moreover, accurate knowledge of the respective SNP energy differences is necessary in this method in order to be able to set the individual electrical conditions such as electrical potential, possibly pulse duration and intensity. The DNA may be damaged through the use of high-energy pulses.

In addition, WO 02/083952 A1 discloses a method for analyzing nucleic acids in a sample, in which an SNP analysis is carried out and a hybridization of the samples takes place at predetermined temperatures. The analysis in this case takes place in particular by way of the so-called FRET (Fluorescence Resonance Energy Transfer) method. The specification of temperature and setting are said in this case to take place in accordance with U.S. Pat. No. 5,965,410 A, which is cited as integral constituent of WO 02/083952 A1. In particular, a specific program with which, when the flow is stationary, the temperature can be set at a defined previously calculated value is indicated therein.

In addition, U.S. Pat. No. 6,391,558 A discloses an electrochemical method for detecting DNA, in which a quantitatively readable electrical signal is generated in the hybridization process.

SUMMARY

It is an object of at least one embodiment of the invention to propose a simple and robust, as well as mild and reversible method which can reliably detect in one operation a plurality of SNPs with different, ideally also unknown, melting temperatures, and/or to create an associated arrangement for carrying out the method.

An object may be achieved according to at least one embodiment of the invention by a sequence of method steps. An associated arrangement may be included for carrying out the method of at least one embodiment of invention.

In at least one embodiment of the invention, measurement is carried out in each case after the temperature holding time is reached with a washing liquid stationary. In this regard there is a crucial difference from the above prior art.

In a specific further development, the method of at least one embodiment of the invention advantageously makes use of the methodology of electrochemical detection, especially of redox cycling in combination with an enzyme label or enzymatic amplification. The enzyme used in this connection preferably has a thermal stability. The DNA capture molecules are located on a solid support material, preferably a silicon chip or an insulator provided with electrodes.

At least one device for monitoring and controlling the temperature of the liquid over the hybridization positions of the chip, and one device for controlling the rate of liquid flow and associated detection device are present on the arrangement of at least one embodiment of the invention. For this purpose, specifically the sensor chip is connected to a microfluidics system including precision pump in at least one embodiment.

BRIEF DESCRIPTION OF THE DRAWINGS

Further details and advantages of the invention are evident from the following description of the figures of example embodiments. These show.

DETAILED DESCRIPTION OF THE EXAMPLE EMBODIMENTS

The intention is to carry out a method for detecting DNA point mutations (SNP analysis) utilizing a binding, i.e. hybridization, of target DNA to be detected to capture DNA which is immobilized position-specifically on a DNA chip:

The procedure for advantageous implementation of the SNP analysis is in particular as follows: a transducer chip, e.g. a silicon chip or other, preferably planar, arrays having at least one hybridization position and preferably electrochemical transducers, e.g. in the form of noble metal microelectrodes, is loaded with at least one type of DNA capture probes. The transducers have, for example, a diameter of 180 μm and a two-dimensional grid size of 200×200 μm. The transducer array has several 10 up to about 100 positions.

To implement SNP analyses, the sequences of the capture probes are selected so that in each case all four possible nucleotide variants of an SNP are spotted. If the melting conditions for a match and mismatch are accurately known it is also possible to operate with a single type of capture probe. It is then possible to conclude whether there is a match or mismatch from the position of the melting curve. In order to be able to detect reliably all three possible analytical situations (1: only match, 2: only mismatch, 3: match combined with mismatch), in the simplest case two measurement positions with respectively match and mismatch capture probes are necessary.

To convert the novel measurement method into practice, the chip is incorporated in a flow cell which makes it possible to have a thin layer of liquid over the hybridization positions of the chip, which form a transducer array or sensor array. Hybridization with the analyte DNA sample, especially a biotinylated PCR product, is carried out at a temperature such that all match hybrids, but also mismatch hybrids, can be produced. Streptavidin-enzyme conjugate is then coupled on via the biotinylated target DNA.

A solution with the substrate specific for the enzyme is then pumped over the sensor chip. The pump is stopped for, for example, 5-10 s, preferably at constant temperature, and the initial gradient of the increase in current is measured. The increase in current results from the fact that the label enzyme (e.g. a thermostable esterase) converts the enzyme substrate (corresponding to the enzyme, e.g. p-aminophenyl acetate), the reaction product produced there from (corresponding to p-aminophenol) is electrochemically converted at the transducer electrodes, and thus an electric current proportional to the reaction product is generated. The increase in the electric current results from the fact that the enzyme continuously replenishes reaction product at the site of the binding and thus an increase in the product concentration takes place, accompanied by an increase in the electric current.

It should be emphasized that the reaction product to be detected (e.g. p-aminophenol) is liberated on the bound label enzyme and is able to diffuse freely or may be flushed away with the stream of enzyme substrate liquid. Detection by devices/methods, for example of electrochemical conversion at electrodes or through optical detection, e.g. by measurement of absorption of suitable optically active reaction products, can take place only if the flow rate of the enzyme substrate solution for the detection is markedly reduced or preferably set equal to zero.

Operation of the liquid pump is then resumed (a few μl/min) and, at the same time, there is a defined increase in the temperature by a few ° C., e.g. 2° C. This measure leads firstly to removal of the enriched reaction products from the detection sites, and secondly the mismatch target-capture DNA hybrids can be dissolved by increasing the temperature, and thus melting, and be transported away from the hybridization and detection positions. This leads firstly to the previously increased electrochemical signals being set back again (not necessarily to zero, but merely markedly reduced) and secondly to prevention of rehybridization of the mismatched target DNA with the capture DNA because of the reduction in concentration. Further measurements are made possible only by the sensor signals which have been set back. For this purpose, the pump is stopped again after some seconds, e.g. 20 s, for, for example, 5-10 s, and the increase in current is again recorded.

The above procedures are repeated until all the DNA target molecules have been removed in accordance with their melting points successively from the capture probes. The melting curves obtained thereby, i.e. the increases in current of all transducer positions as a function of the temperature, are analyzed. This takes place in particular under computer control according to a predetermined software program.

The overall method of at least one embodiment is complete after about 10 min and thus represents by comparison with the prior art a particularly fast method which, owing to the use of enzymatic amplification, exhibits high sensitivity and therefore also high reliability.

A typical temperature range for recording the melting curves described above is about 40° C. to 70° C. Since enzymes, especially the label enzymes known from the literature, are generally stable only up to about 40° C., i.e. denature above this temperature and thus lose their catalytic action required for the measurement, thermostable enzymes are employed in particular according to the invention, such as, for example, a thermostable esterase.

Figure 1A:
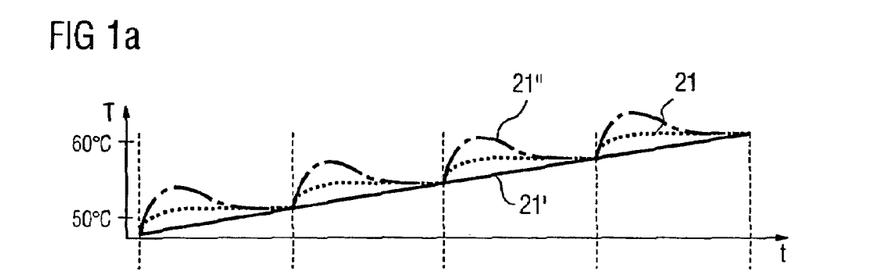
FIGS. 1a, 1b and 1c the procedure for the method of at least one embodiment of the invention with three examples of preset temperature profiles, a liquid flow profile and with a sensor signal from a single hybridization position as a function of time, FIGS. 2 and 3 the analysis or melting curves derived from the sensor signals (current curves) shown in FIG. 1c, with the initial gradients of the current and with the increase in current standardized to the 40° C. signal as a function of the temperature, FIG. 4 a diagrammatic representation of an arrangement for carrying out the method of at least one embodiment, FIG. 5 and FIG. 6 the enlarged representation of two method states in the arrangement shown in FIG. 4, FIG. 7 and FIG. 8 an example embodiment of the optical detection in the described SNP method and FIG. 9 and FIG. 10 an example embodiment of the electrochemically enzymatic variant of the method.
Figure 1B:
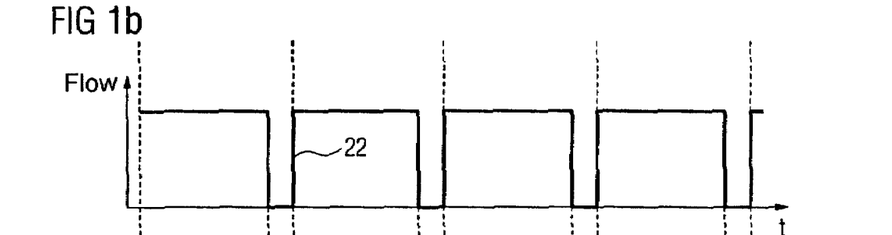
Figure 1C:
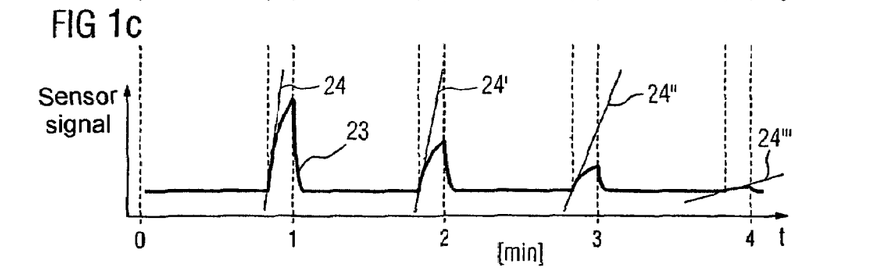

The described measurement method is illustrated by way of FIG. 1. In each of subfigures 1a, 1b, 1c the time is plotted as abscissa on the same scale, and in FIG. 1a the temperature between 50° C. and 60° C. is plotted as ordinate, and in FIG. 1b the flow is plotted in unscaled units, and in FIG. 1c the sensor signal (redox cycling current) is plotted.

It is evident that the temperature is increased in predeterminable steps or linearly, with the flow being changed in correlation (synchronously) therewith. The flow is preferably changed, in particular set at zero, in each case after a constant temperature has been set up. When the melting temperature of the capture-target DNA hybrid is reached, the target DNA, including the enzymatic label, will be detached from the capture DNA according to the laws of random distribution, and will be removed by the liquid stream from the respective transducer position and preferably washed into a waste container.

The target-capture DNA hybrids whose melting temperature is not yet reached remain at their hybridization position. The washing liquid contains enzyme-specific substrate which is converted by the enzyme labels which are still bound to the product which in turn, owing to the changed flow (in particular set equal to zero), accumulates at the hybridization positions, diffuses to the sensor electrodes and can be detected electrochemically.

In FIG. 1c there is thus evidently a significant increase in the measured current which characterizes in each case the intact hybridization of a capture/target DNA pair. The initial gradient of the increase in current is used in particular for the analysis. When the temperature is increased and the flow returns to the initial value, a new liquid reaches the hybridization positions, whereupon furthermore molecules of the same measurement point or first molecules from other measurement points with higher melting temperature are melted and washed away.

Instead of increasing the temperature in ramp steps in accordance with curve 21, it is possible where appropriate for a temperature increase to take place also continuously or according to a predetermined profile as shown in curves 21' and 21", respectively. The flow corresponding to curve 22 need not necessarily be stopped, but only changed significantly. Profile curves 21, 22 coordinated with each other result in each case as variable.

Figure 2:
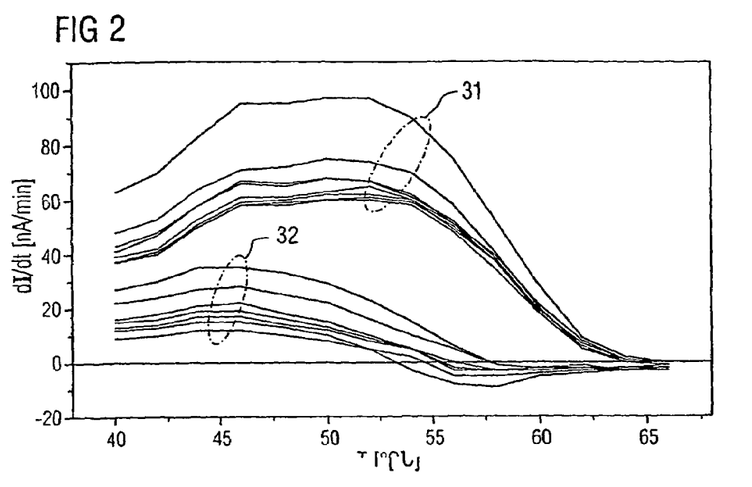

In at least one embodiment, it is essential in each case to set up a stationary or quasistationary state. In FIG. 1c, the sensor signal which is measured for example as current level is designated by 23 and specific values of the gradient of the sensor signal are designated by 24. FIG. 2 shows the melting curves 31, 32 of a plurality of match (31) and a plurality of single base mismatch (32) hybridization positions for a factor V PCR product which were measured at the position-specific transducers according to FIG. 1c, where the increase in current dI/dt is plotted in nA/min as a function of the temperature.

Figure 3:
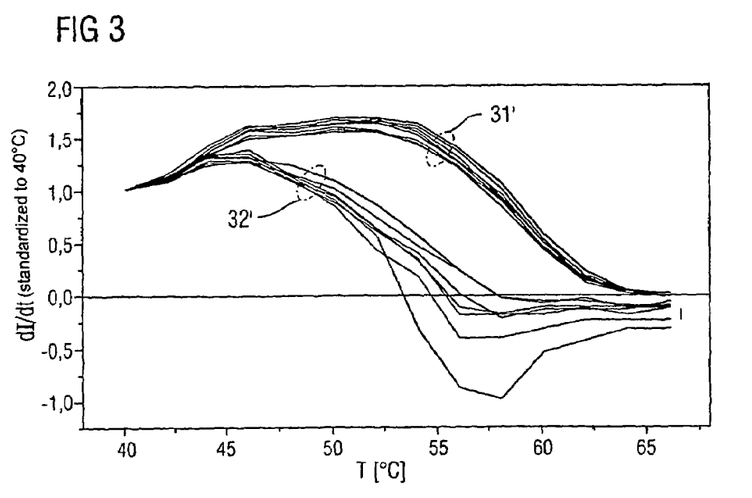

FIG. 3 shows the standardized measurements from FIG. 2 increase in current (T)/increase in current (T=40° C.) as curves 31' and 32', so that the individual curves are comparable. The factor V and the factor V PCR product is a gene important for blood coagulation.

Specifically, the initial gradients of the measured currents (dI/dt) are plotted as a function of the temperature set in each case in FIGS. 2 and 3, as in the example of a transducer or measurement position from FIG. 1c. Significant, in particular sigmoidal curve profiles, 31, 32, resembling titration curves, result for individual capture/target DNA pairs. The essential point in this connection is that the signal profile is significantly different, or the curve has a different position along the abscissa, for matching capture/target DNA pairs compared with mismatching capture/target DNA pairs. In particular, the melting process and, associated therewith, the fall in the melting curve occurs at higher temperatures with matching pairs than with mismatching capture/target DNA pairs.

Figure 4:
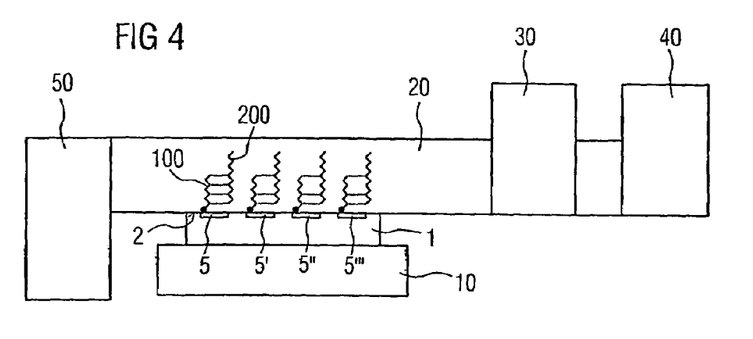

FIG. 4 depicts a general arrangement having a specifically used measurement setup consisting of a chip with a plurality of hybridization positions 5, 5', ..., 5''': in FIG. 4, a so-called DNA chip as known in the art is designated by 1.

Such a DNA chip 1 has on its surface 2 a multiplicity of measurement positions 5, 5', ..., 5''', for example in array form. Capture DNA molecules are arranged immobilized at each measurement position 5, 5', ..., 5''', for example the capture DNA 100 at immobilization point 6. A target DNA 200 can anneal onto the capture DNA 100. The target DNA 200 can be provided with a label. The label may be an enzyme as biocatalytic label, in which case the enzyme label preferably comprises a thermostable enzyme.

The individual measurement points for the immobilization of the capture DNA 100 are designated by 5, 5', ..., 5''', in all subsequent figures. Amplifying and measuring structures, which are generally designated by 3, can preferably be already introduced in chip 1, which is formed from silicon or another semiconductor material. However, chip 1 may also include an insulating material with metallic electrodes without integrated signal processing.

A device 10 for accurate setting of temperature or controlling of temperature is assigned to the measuring chip 1. Suitable for this purpose are, for example, Peltier elements or the like. A temperature measurement takes place on the chip and/or where appropriate on the device for controlling the temperature.

The surface 2 as measurement side of the chip 1 faces a flow channel 20 through which all the substances necessary for the analytical process, such as target DNA 200 and, where appropriate, labeling enzyme, or washing liquid with, where appropriate, enzyme-specific substrate S from a reservoir 40, are fed with a predetermined flow. A flow control 30 which maintains an accurate flow in each case for a predetermined time interval and which ensures a defined flow stop, and in addition a receiving or waste container 50 for substances no longer required, are present.

It is possible in particular with the arrangement described by way of FIG. 4 to guide a washing liquid provided with enzyme substrate S as a thin liquid layer over the chip with precise temperature monitoring. Moreover, predeterminable flow monitoring and accurate measurement and analysis is possible.

Figure 5:
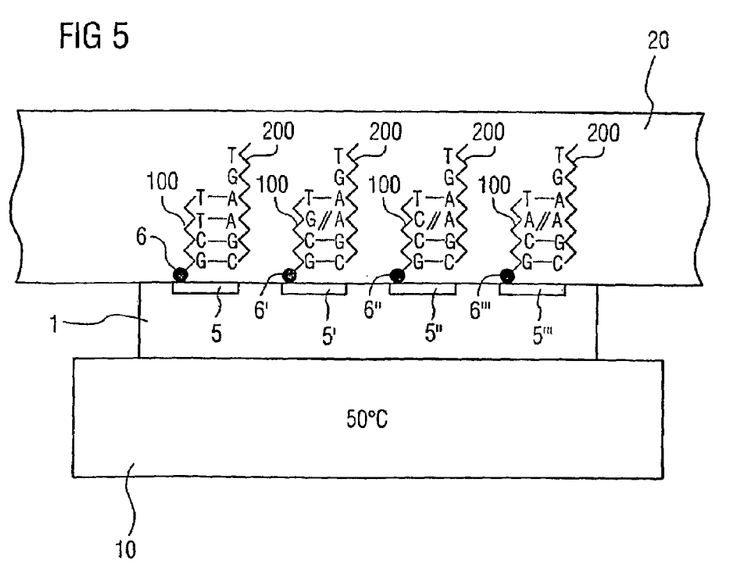
Figure 6:
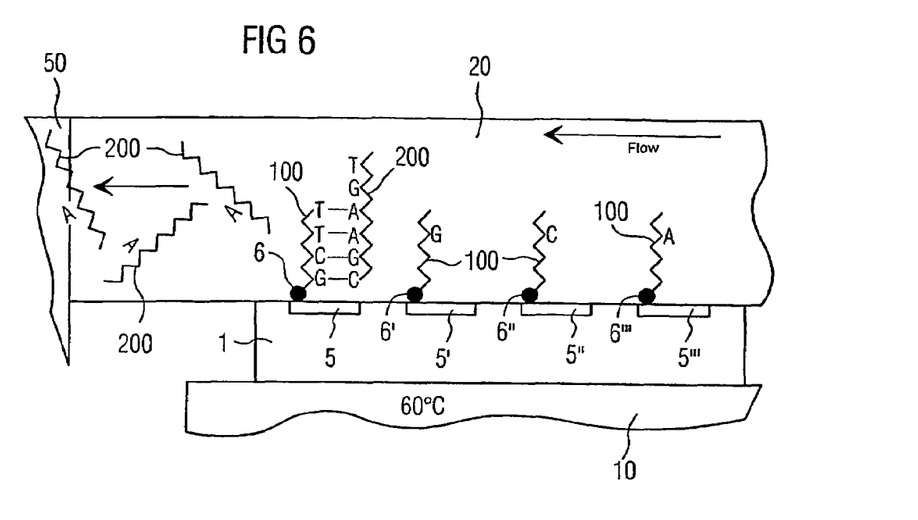

FIGS. 5 and 6 depict two method states in general form based on chip 1, the associated thermostat device 10 and the flow channel 20. The capture DNA 100 and the target DNA 200 with the individual polymorphisms and the associated point mutations are depicted in enlarged representation. It is evident in particular that, for example at a temperature of 50° C., all the captors 100 bind the target DNA 200, with in particular the so-called match bindings A-T, G-C but also the mismatch bindings G//A, C//A and A//A being present. It is evident that the match bindings are stronger than the mismatch bindings.

Specifically, FIG. 6 depicts a state with a thermostat device at, for example, 60° C., the mismatch bindings being melted at this temperature, so that the mismatch target DNA are subsequently washed away. The washed away target DNA molecules can be flushed as far as the waste container 50. However, it is also sufficient for the washed away target DNA molecules to be removed only a small distance from the measurement position, so that they can no longer be detected by any measurement position.

The melting of the mismatch bindings can be detected and analyzed in a position-specific manner as a function of the temperature. Two alternative measurement possibilities therefore are depicted in FIGS. 7/8 on the one hand and in FIGS. 9/10 on the other hand.

Figure 7:
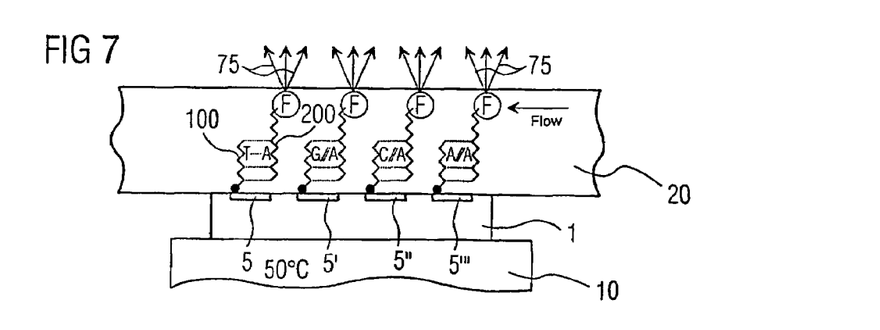
Figure 8:
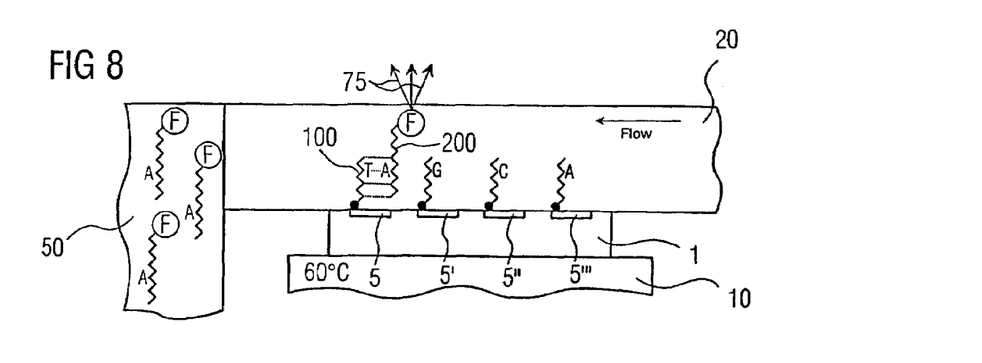

FIGS. 7 and 8 are derived from FIGS. 4 and 5/6, respectively, the target DNA 200 being provided with a fluorescent label F. Optical reading is possible with such fluorescence-labeled target DNA 200. The optical signals 75 are picked up and analyzed in a positionally accurate manner with a spectrometer which is not depicted in detail in FIGS. 7 and 8.

It is clearly evident from comparison of FIGS. 7 and 8 that when the melting temperature is exceeded, for example at the temperature of 60° C., the mismatch bindings are melted and the relevant target DNA 200, including the fluorescent label F, are washed away. A reduced signal thus results at the mismatch positions.

The preferred, alternative enzymatic/electrochemical measurement makes use of an enzymatically catalyzed reaction to form a product P, for which the following equation applies:

$$S \xrightarrow{E} P,$$

where S is an enzyme substrate, E is an enzyme label and P is the reaction product.

Figure 9:
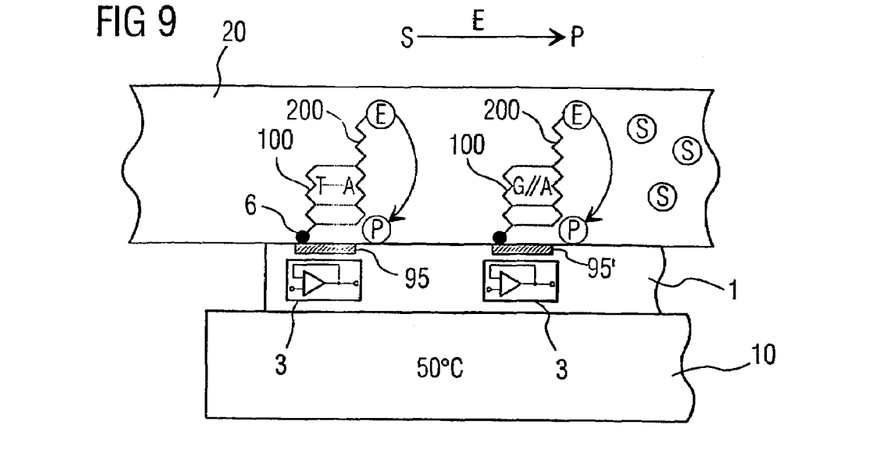

In FIG. 9, the target DNA molecules 200 are provided with the enzyme label E, with the arrows indicating the enzymatically catalyzed reaction and the diffusion of the reaction products P to the electrical measurement positions. Electrochemical signal receivers or transducers 95, 95' are present at the measurement positions 5, 5', ..., 5''', of the chip 1, it being possible in conjunction with the previously mentioned signal processing structures 3 in the silicon of the chip 1 for an electrical signal such as, for example, a current, which represents a measure of the concentration of the reaction product P, to be picked up directly.

Figure 10:
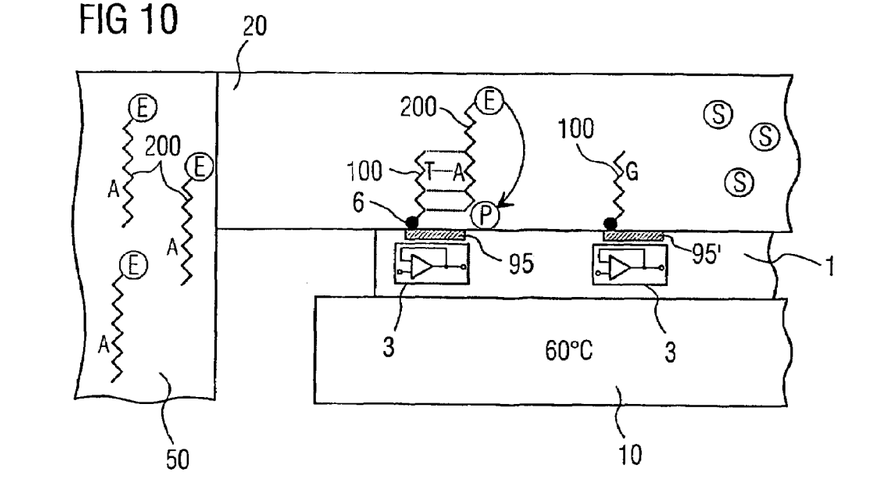

In FIG. 9 and FIG. 10, corresponding to FIGS. 7 and 8, the two states are shown once again at a temperature of 50° C. and at a temperature of 60° C. The results are thus comparatively large electrical signals in the first state, due to conversion of S into P at all the measurement positions, and reduced or no signals at the mismatch positions, but a comparatively large electrochemical signal at the match position, in the second state. The washed away target DNA molecules, and washed away reaction product P can again be flushed as far as the waste container 50. However, it may also be sufficient to remove the washed away target DNA molecules and reaction products only a small distance from the measurement positions, so that they can no longer be detected by any of the available measurement positions.

A particular advantage of the enzymatic/electrochemical method is the fact that, in contrast to, for example, optical methods, it is substantially independent of a background signal, because the increase in current dI/dt is used for the analysis, and not the absolute current signal itself. This makes it unnecessary for the enzyme-labeled target DNA, and the reaction product P generated thereby, to be washed as far as the waste container. It is merely necessary for the concentration of the reaction product P specifically at the measurement positions to be eliminated by brief washing. It is thus also sufficient in the following washing processes for the washing liquid merely to be pumped backward and forward, and it is thus possible to save washing liquid, which is advantageous especially for integrated and miniaturized embodiments.

The current signals correspond to the peaks in FIG. 1c, with their initial gradients dI/dt corresponding to the lines 24, 24', 24", ... from FIG. 1c being analyzed in FIGS. 2 and 3.

Besides the two examples with a detection by optical or enzymatic labels, it is also possible for there to be label-free detection of the bound target DNA 200. In the optical label-free detection, the intrinsic changes in the UV absorption on melting of the DNA double strands are picked up. In the electrical label-free detection, by contrast, use is made of the process of intrinsic guanine oxidation. A further label-free detection is possible by way of electrochemical impedance methods. A further possibility is also label-free detection by measurements of the change in mass, i.e. gravimetrically, e.g. by acoustic methods such as surface wave sensors (called SAWs).

It is also possible in the labeling method to employ magnetic labels in combination with magnetic field sensors.

It is essential in the described method of at least one embodiment, for the measurement and associated analysis to be automatable. Is thus possible. The respective flow profile takes place as a function thereof, with firstly the washing away of the melted mismatch bindings when a predetermined temperature is set, and secondly the detection of the position-specific bound target DNA taking place when the washing liquid is "not in motion".

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for detecting DNA point mutations utilizing capture/target DNA hybrids at hybridization positions, the capture/target DNA hybrids formed by binding target DNA to be detected to capture DNA immobilized position-specifically on a DNA chip, the method comprising,
   performing a washing phase and a measurement phase alternately at different temperatures,
   the washing phase including:
   a) passing a washing liquid at a controlled flow rate over the DNA chip,
   b) changing the temperature at the hybridization positions in a defined manner as a function of time, with a continuous increase in temperature as a function of time being carried out in ramps with subsequent temperature holding times, and
   c) melting the capture/target DNA hybrids temperature-dependently, and removing melted target DNA from the hybridization positions using the flowing washing liquid, such that non-melted target DNA remains on the DNA chip,
   the measurement phase including:
   d) stopping the flow of washing liquid during the temperature holding times,
   e) position-specifically detecting the non-melted target DNA at a current temperature of the temperature holding time, and
   f) analyzing signals according to a predetermined program, the analyzed signals being used to detect the DNA point mutations.

2. The method as claimed in claim 1, wherein method steps a) to e) are repeated more than once.

3. The method as claimed in claim 1, wherein the detection of the non-melted target DNA takes place label-free.

4. The method as claimed in claim 3, wherein the label-free detection takes place optically.

5. The method as claimed in claim 4, wherein the optical detection makes use of an intrinsic change in the UV absorption based on melting of DNA double strands.

6. The method as claimed in claim 3, wherein label-free detection takes place electrically.

7. The method as claimed in claim 6, wherein the label-free detection takes place by way of an intrinsic guanine oxidation process.

8. The method as claimed in claim 7, wherein the label-free detection takes place by way of electrochemical impedance methods.

9. The method as claimed in claim 7, wherein the label-free detection takes place gravimetrically.

10. The method as claimed in claim 1, wherein the detection of the non-melted target DNA takes place with use of a label.

11. The method as claimed in claim 10, wherein the detection takes place by use of an optical label.

12. The method as claimed in claim 10, wherein the detection takes place by use of a magnetic label.

13. The method as claimed claim 10, wherein the detection takes place by use of an enzymatic label.

14. The method as claimed in claim 13, wherein the washing liquid includes enzyme substrate.

15. The method as claimed in claim 14, wherein an active enzyme, which is stable in the temperature range used, is used.

16. The method as claimed in claim 13, wherein the enzymatic label catalyzes an optically detectable reaction.

17. The method as claimed in claim 13, wherein the enzymatic label catalyzes an electrochemically detectable reaction.

18. The method as claimed in claim 17, wherein the electrochemical detectable reaction is detectable using a redox cycling-amplified current measurement.

19. The method as claimed in claim 10, wherein a change in a concentration of at least one of a substrate and a product is detected and analyzed.

20. The method as claimed in 1, wherein the analysis and representation of the signal takes place as a function of temperature.

21. The method as claimed in claim 20, wherein a melting curve is standardized to a defined temperature in the analysis.

22. The method as claimed in claim 1, wherein the analysis is computer-controlled.

23. The method as claimed in claim 22, wherein the analysis is carried out by software.

* * * * *